United States Patent
Messing

(10) Patent No.: US 8,428,888 B2
(45) Date of Patent: Apr. 23, 2013

(54) SIGNAL PROCESSING ALGORITHMS FOR IMPEDANCE BIOSENSOR

(75) Inventor: Dean Messing, Camas, WA (US)

(73) Assignee: Sharp Laboratories of America, Inc., Camas, WA (US)

( * ) Notice: Subject to any disclaimer, the term of this patent is extended or adjusted under 35 U.S.C. 154(b) by 529 days.

(21) Appl. No.: 12/661,127

(22) Filed: Mar. 10, 2010

(65) Prior Publication Data

US 2011/0221458 A1  Sep. 15, 2011

(51) Int. Cl.
*G01N 33/50* (2006.01)

(52) U.S. Cl.
USPC ............. 702/32; 702/22; 205/777.5; 600/345

(58) Field of Classification Search ............ 204/403.01–403.15; 205/777.5, 778, 792; 600/345–348; 435/4–40.52; 422/68.1–98; 436/67–71, 500–548; 702/22–32; 324/600–724

See application file for complete search history.

(56) References Cited

U.S. PATENT DOCUMENTS

| | | | |
|---|---|---|---|
| 6,990,422 B2 | 1/2006 | Laletin et al. |
| 7,090,764 B2 | 8/2006 | Iyengar et al. |
| 7,373,255 B2 | 5/2008 | Karlsson et al. |
| 2005/0131650 A1 | 6/2005 | Andersson et al. |
| 2007/0016378 A1 | 1/2007 | Andersson |

FOREIGN PATENT DOCUMENTS

| | | |
|---|---|---|
| WO | 03069304 A2 | 8/2003 |
| WO | 2008138553 A1 | 11/2008 |

OTHER PUBLICATIONS

International Search Report dated Jun. 28, 2011 in PCT International Patent App. No. PCT/JP2011/056138, filed Mar. 9, 2011, Sharp Kabushiki Kaisha, 7 pgs.

*Primary Examiner* — J. Christopher Ball
(74) *Attorney, Agent, or Firm* — Chernoff Vilhauer McClung & Stenzel, LLP

(57) ABSTRACT

A method for determining impedance includes receiving a time varying voltage signal from a biosensor and receiving a time varying current signal from the biosensor. The time varying voltage signal and the time varying current signal are transformed to a domain that represents complex values. The impedance representative of the biosensor based upon the transformed time varying voltage signal and the time varying current signal is calculated.

21 Claims, 16 Drawing Sheets

From Biosensor System to Medical Diagnosis

FIG 1. From Biosensor System to Medical Diagnosis $$|Z|(t) = B - Ae^{-st} \overbrace{+ \nu(t)}^{\text{noise}} \text{ where } s, A, B \geq 0 \text{ are constants.}$$

Typical noisy impedance signal and impedance model function without noise.

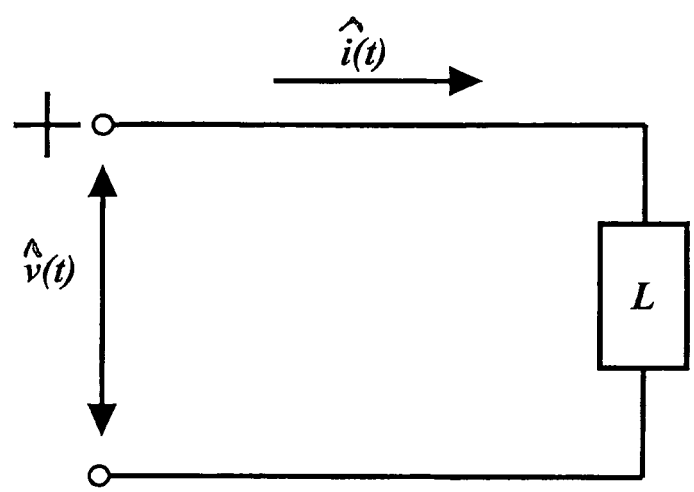
FIG 3. One-port linear time-invariant system $L$, driven by voltage $\hat{v}(t)$ with resultant current $\hat{i}(t)$.

Ten instances of y(n) as defined by equation 5, where N = 64, M = 3.
Complex frequencies are:
$\beta_1 = -0.05 + i2\pi 0.37$, $\beta_2 = -0.10 + i2\pi 0.14$, and $\beta_3 = -0.15 - i2\pi 0.30$.
Complex amplitudes are:
$\alpha_1 = 0.5e^{i2\pi 0.30}$  $\alpha_2 = 0.8e^{i2\pi 0.65}$  $\alpha_3 = 1.1e^{i2\pi 0.11}$
PSNR ≈ 15dB.

FIG. 6. Zeros of B(z) as delivered by KT algorithm for each of the ten noisy signal instances of FIG. 5, plotted in the z-transform domain.

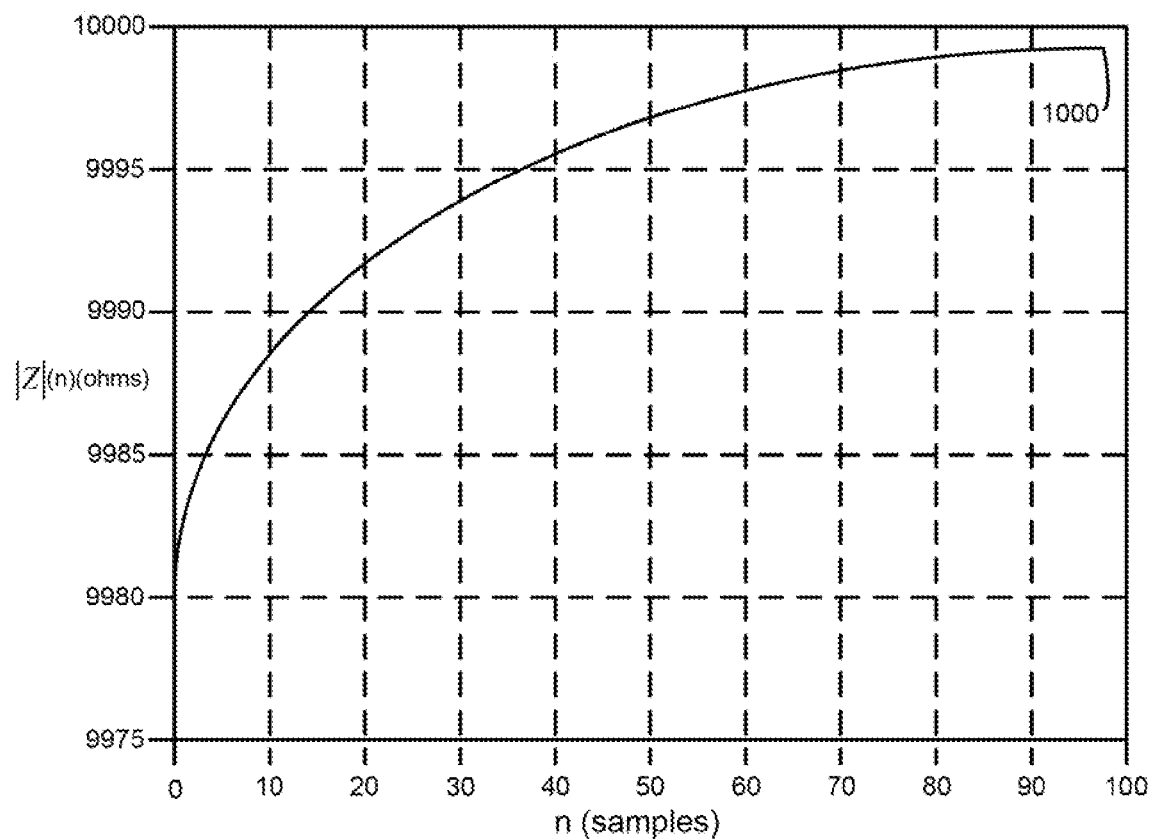
FIG. 10. Graph of Eq. 9; graph of estimated model defined by Eq. 9.

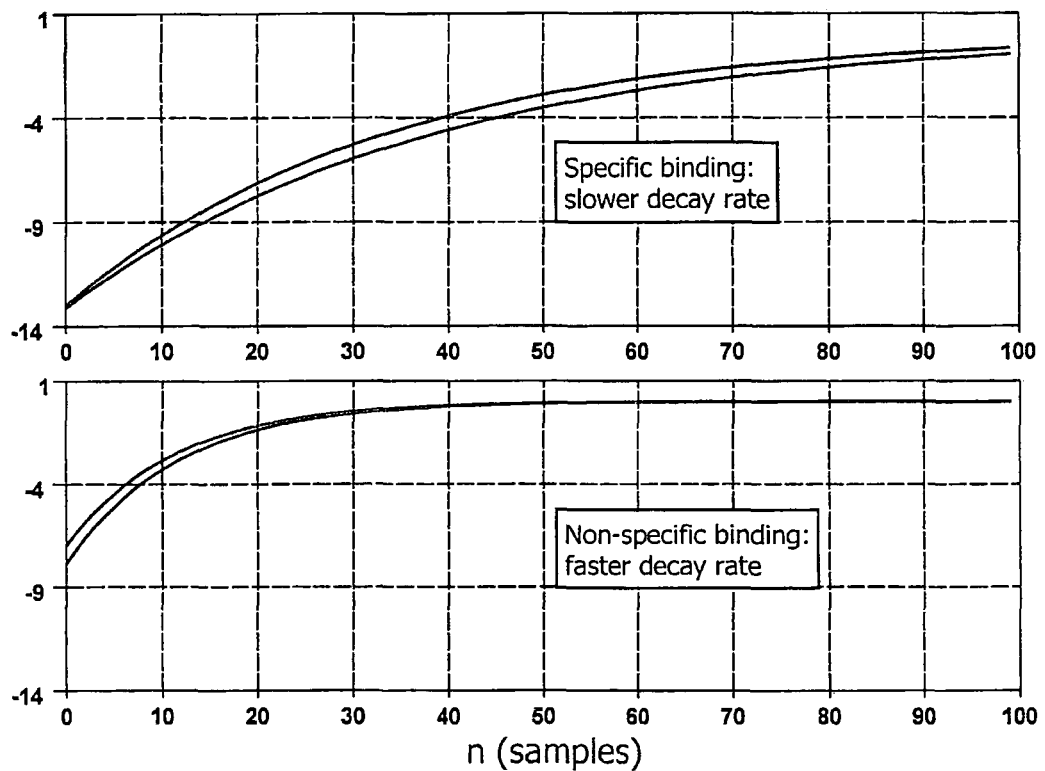
FIG 11. Graphs of the second and third terms, respectively, of Eq. 9; graphs of estimated second and third terms, respectively, using the model parameters of Eq. 9 returned by the algorithm.

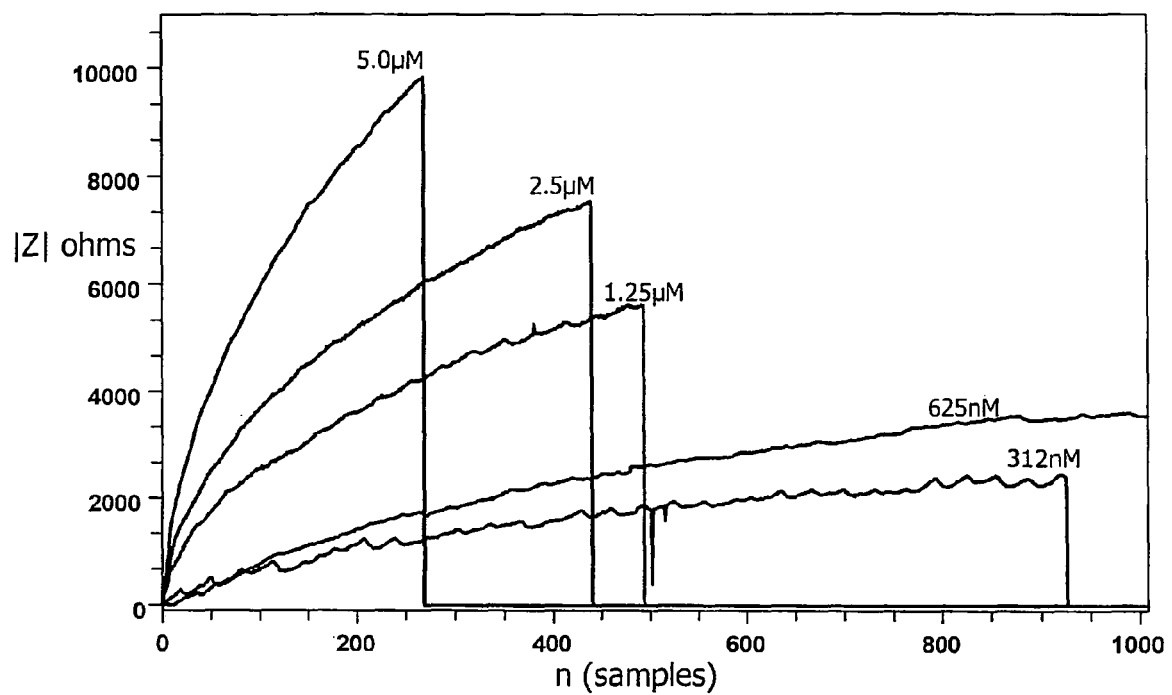
FIG 12. Aligned impedance responses for an oligonuclueotide titration series.

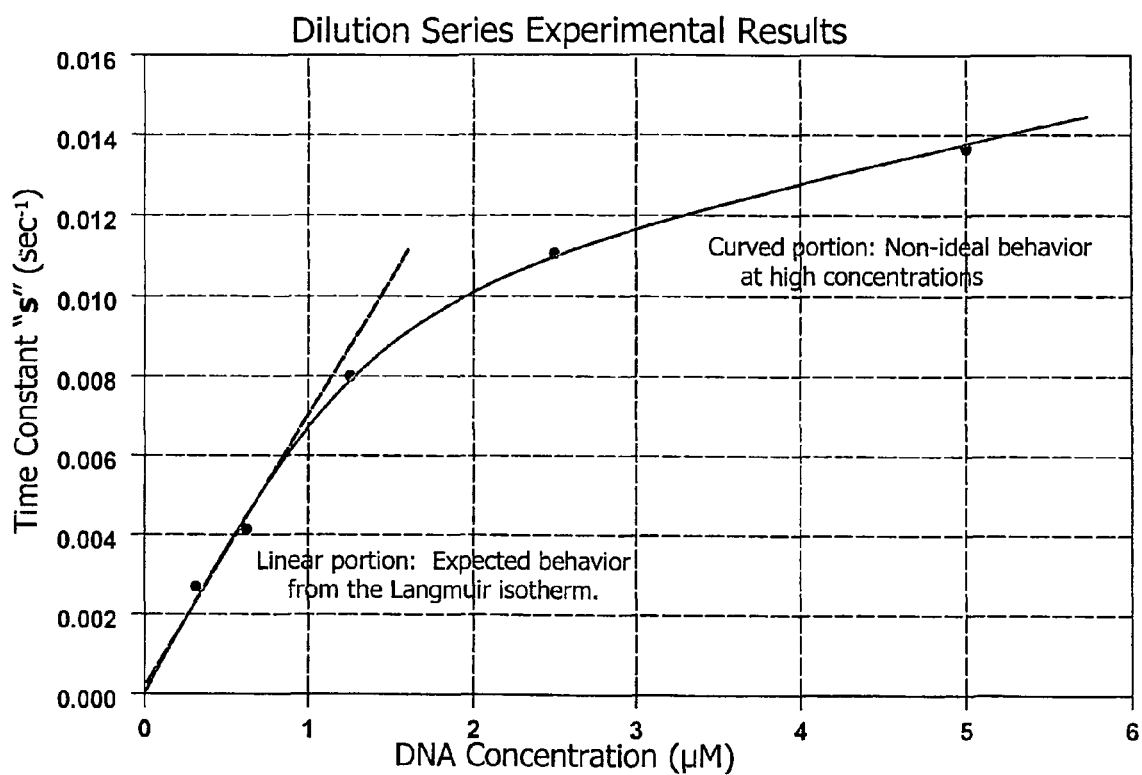
FIG. 14. Results of estimating s for each analyte concentration in the titration series. The estimated model value of s is plotted against the concentration in $\mu$-molar units.

SIGNAL PROCESSING ALGORITHMS FOR IMPEDANCE BIOSENSOR

CROSS-REFERENCE TO RELATED APPLICATIONS

Not applicable.

BACKGROUND OF THE INVENTION

The present invention relates generally to signal processing for a biosensor.

A biosensor is a device designed to detect or quantify a biochemical molecule such as a particular DNA sequence or particular protein. Many biosensors are affinity-based, meaning they use an immobilized capture probe that binds the molecule being sensed—the target or analyte—selectively, thus transferring the challenge of detecting a target in solution into detecting a change at a localized surface. This change can then be measured in a variety of ways. Electrical biosensors rely on the measurement of currents and/or voltages to detect binding. Due to their relatively low cost, relatively low power consumption, and ability for miniaturization, electrical biosensors are useful for applications where it is desirable to minimize size and cost.

Electrical biosensors can use different electrical measurement techniques, including for example, voltammetric, amperometric/coulometric, and impedance sensors. Voltammetry and amperometry involve measuring the current at an electrode as a function of applied electrode-solution voltage. These techniques are based upon using a DC or pseudo-DC signal and intentionally change the electrode conditions. In contrast, impedance biosensors measure the electrical impedance of an interface in AC steady state, typically with constant DC bias conditions. Most often this is accomplished by imposing a small sinusoidal voltage at a particular frequency and measuring the resulting current; the process can be repeated at different frequencies. The ratio of the voltage-to-current phasor gives the impedance. This approach, sometimes known as electrochemical impedance spectroscopy (EIS), has been used to study a variety of electrochemical phenomena over a wide frequency range. If the impedance of the electrode-solution interface changes when the target analyte is captured by the probe, EIS can be used to detect that impedance change over a range of frequencies. Alternatively, the impedance or capacitance of the interface may be measured at a single frequency.

What is desired is a signal processing technique for a biosensor.

The foregoing and other objectives, features, and advantages of the invention will be more readily understood upon consideration of the following detailed description of the invention, taken in conjunction with the accompanying drawings.

BRIEF DESCRIPTION OF THE SEVERAL VIEWS OF THE DRAWINGS

FIG. 3 illustrates a one-port linter time invariant system.
FIG. 10 illustrates an impedance graph.
FIG. 11 illustrates groups of specific binding and non-specific binding.
FIG. 12 illustrates aligned impedance responses.
FIG. 14 illustrates estimation of analyte concentration.

DETAILED DESCRIPTION OF PREFERRED EMBODIMENT

Figure 1:
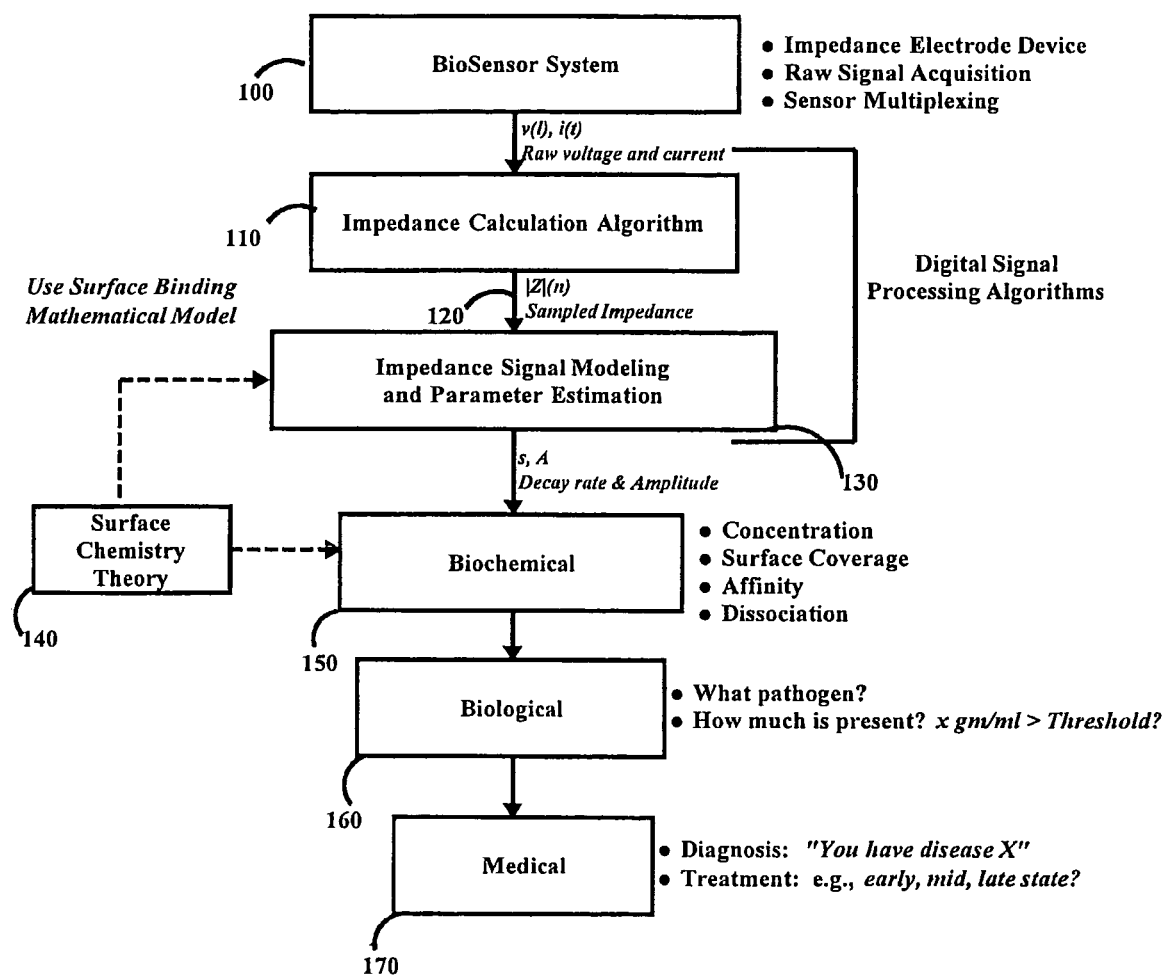
FIG. 1 illustrates a biosensor system for medical diagnosis.

Referring to FIG. 1, the technique used during an exemplary medical diagnostic test using an impedance biosensor system as the diagnostic instrument is shown. The system includes a bio-functionalized impedance electrode and data acquisition system 100 for the signal acquisition of the raw stimulus voltage, v(t), and response current, i(t). Next, an impedance calculation technique 110 is used to compute sampled complex impedance, Z(n) as a function of time.

As illustrated in FIG. 1, the magnitude of the complex impedance, |Z(n)|, is shown as the output of the impedance calculation technique 110. Preferably, a parameter estimation technique 130 uses |Z|(n) 120 as its input. Real or imaginary parts, or phase of Z are also possible inputs to the parameter estimation technique 130. Following the computation of |Z|(n) 120, the parameter estimation technique 130 extracts selected parameters. Such parameters may include, for example, an amplitude "A", and decay rate "s". The amplitude and decay rate may be modeled according to the following relation:

$$|Z(n)| = B - A e^{-sn} \text{ where } s, A, B \geq 0 \text{ are preferably constants} \quad \text{(equation 1)},$$

derived from surface chemistry interaction 140. The constant B preferably represents the baseline impedance which may also be delivered by the parameter estimation technique. The surface chemistry theory 140 together with the results of the parameter estimation 130 may be used for biochemical analysis 150. The biochemical analysis 150 may include, for example, concentration, surface coverage, affinity, and dissociation. The result of the biochemical analysis 150 may be used to perform biological analysis 160. The biological analysis 160 may be used to determine the likely pathogen, how much is present, whether greater than a threshold, etc. The biological analysis 160 may be used for medical analysis 170 to diagnosis and treat.

Figure 2:
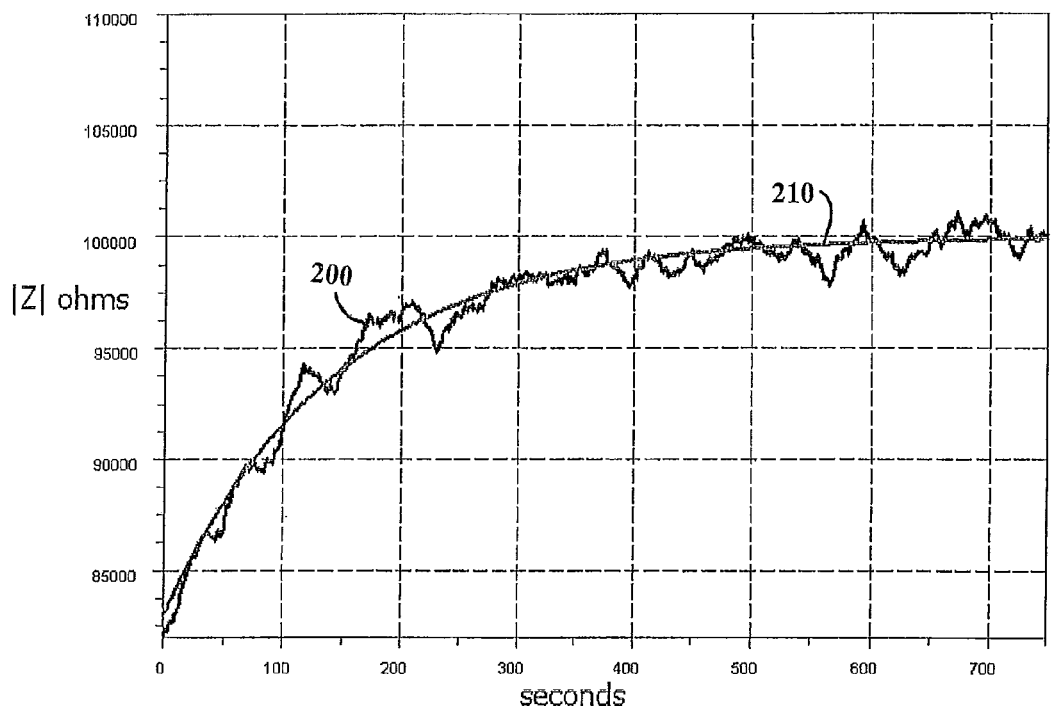
FIG. 2 illustrates a noisy impedance signal and impedance model.

Referring to FIG. 2, an exemplary noisy impedance signal 200 is shown during analyte binding. The parameter estimation 130 receives such a signal as an input and extracts s, A, and B. From these three parameters, an estimate of the underlying model function may be computed from equation 1 using the extracted parameters. Such a model function is shown by the smooth curve 210 in FIG. 2. One of the principal difficulties in estimating these parameters is the substantial additive noise present in the impedance signal 200.

Over relatively short time periods, such as 1 second or less, the system may consider the impedance of the biosensor to be in a constant state. Based upon this assumption, it is a reasonable to approximate the system by a linear time invariant system such as shown in FIG. 3. Variables with a "hat" are complex valued, while the complex impedance is noted as Z. In some embodiments, for example, the system may be non-linear, time variant, or non-linear time variant.

One may presume that FIG. 3 is driven by the complex exponential voltage $\hat{v}(t) = \hat{A}_v e^{j\omega_0 t}$ (equation 2) where $\hat{A}_v$ is a complex number known as the complex amplitude of v(t), and $\omega_0$ is the angular frequency of v(t) in rad/sec. The current through L will, again, be a complex exponential having the same angular frequency $\hat{i}(t)=\hat{A}_i e^{j\omega_0 t}$ (equation 3) where $\hat{A}_i$ is the complex amplitude of $\hat{i}(t)$. The steady-state complex impedance Z of L at angular frequency $\omega_0$ is defined to be the quotient $\hat{v}(t)/\hat{i}(t)$ when the driving voltage or current is a complex exponential of frequency $\omega_0$. This definition does not hold for ordinary real-valued "physical" sinusoids. This may be observed, for example, from the fact that the denominator of v(t)/i(t) would periodically vanish if v(t) and i(t) are sine curves. Denoting $\hat{A}_v = A_v e^{j\theta}$ and $\hat{A}_i = A_i e^{j\theta}$, where $A_v = |\hat{A}_v|$ and $A_i = |\hat{A}_i|$ then Z becomes $$Z = \frac{A_v}{A_i} e^{j(\phi-\theta)}. \quad \text{(equation 4)}$$

The impedance biosensor delivers sampled voltage and current from the sensor. It is noted that the sinusoidal (real-valued) stimulus voltage and response current can each be viewed as the sum of two complex exponential terms. Therefore to estimate the complex voltage and the complex current for calculating Z, the system may compute the discrete-time-Fourier-transform ("DTFT") of each, where the DTFT of each is evaluated at a known stimulus frequency. If the stimulus frequency is not known, it may be estimated using standard techniques. Unfortunately, the finite time aperture of the computation and the incommensurability of the sampling frequency and the stimulus frequency can corrupt the estimated complex voltage and current values.

Figure 4A:
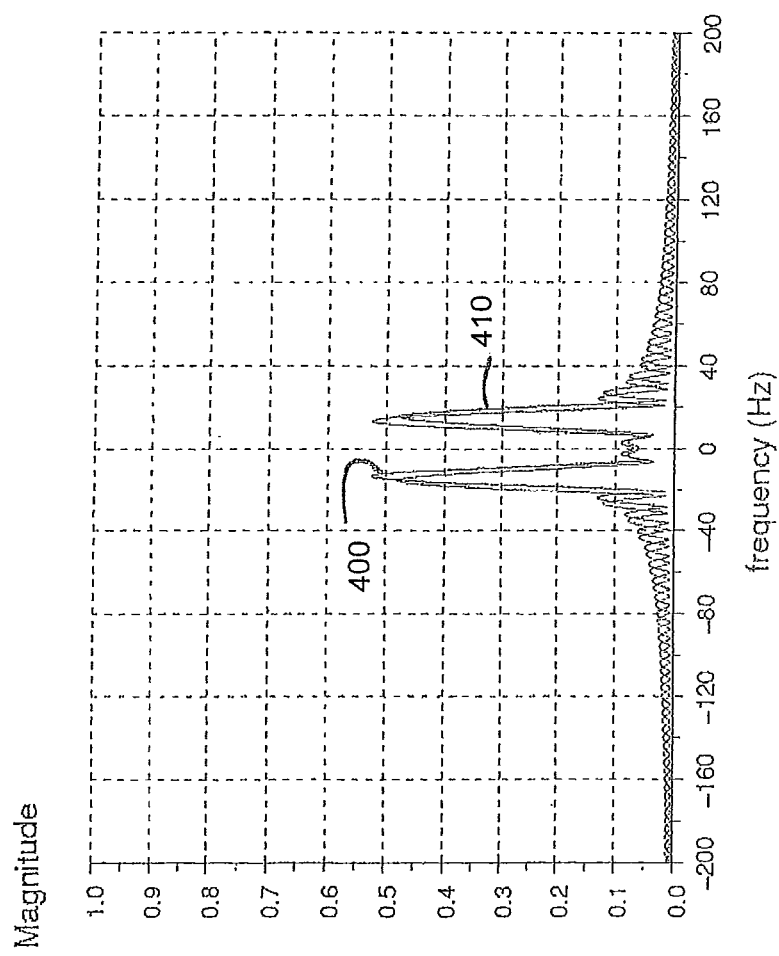
FIGS. 4A and 4B illustrate different pairs of DTFT functions.
Figure 4B:
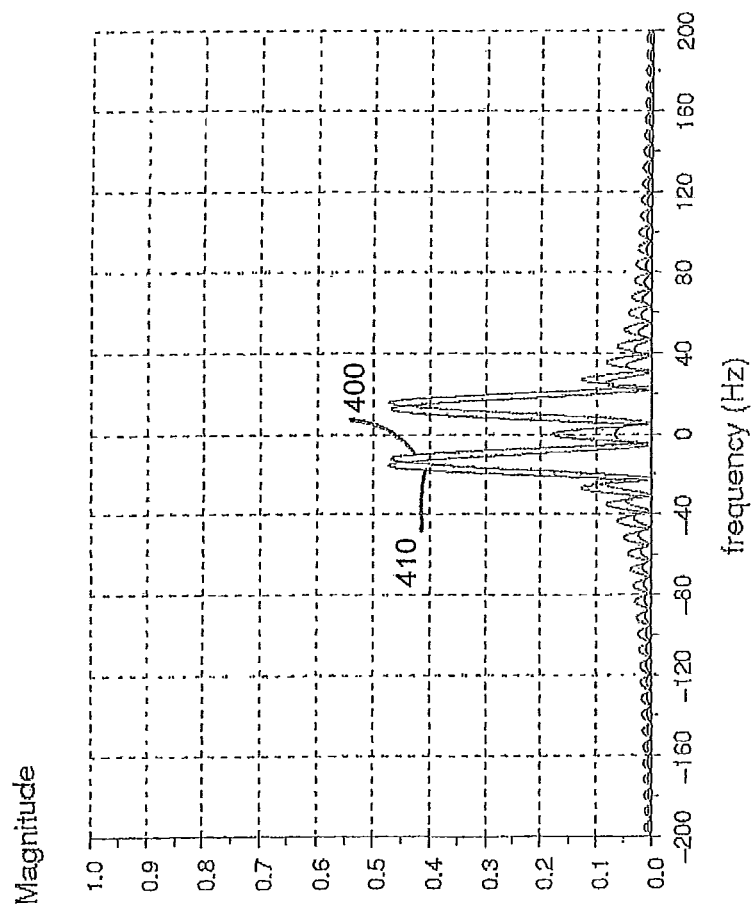

An example of these effects are shown in FIGS. 4A and 4B where the DTFT of two sinusoids having different frequencies and phases, but identical (unit) amplitudes are plotted. FIG. 4A illustrates a plot of the DTFT of a 17 Hz sinusoid 400 and a 19 HZ sinusoid 410. Each has the same phase, $\psi$. FIG. 4B illustrates a shifted phase of each to a new value $\psi \neq \phi$. It may be observed that the peak amplitudes of the DTFTs are different in one case and nearly the same in the other, yet the actual amplitudes of the sinusoids are unity in all cases.

A correction technique is used to determine the "true" value of the underlying peak from the measured value of the positive frequency peak together with the contribution of the negative frequency peak weighted by a value, such as the Dirichlet Kernel function associated with the time aperture. The result is capable of giving the complex voltage and current estimated values within less than 0.1% of their "true" values. Once the estimates of $\hat{v}$ and $\hat{i}$ are found, Z is computed as previously noted.

The decay rate estimation technique may use any suitable technique. The preferred technique is a modified form of the general Kumaresan-Tufts (KT) technique to extract complex frequencies. In general, the KT technique assumes a general signal model composed of uniformly spaced samples of a sum of M complex exponentials corrupted by zero-mean white Gaussian noise, w(n), and observed over a time aperture of N samples. This may be described by the equation $$y(n) = \sum_{k=1}^{M} \alpha_k e^{\beta_k n} + w(n) \quad \text{(equation 5)}$$

$$n = 0, 1, \ldots, N-1.$$

$\beta_k = -s_k + i2\pi f_k$ are complex numbers ($s_k$ is non-negative) and $\alpha_k$ are the complex amplitudes. The $\{\beta_k\}$ may be referred to as the complex frequencies of the signal. Alternatively, they may be referred to as poles. $\{s_k\}$ may be referred to as the pole damping factors and $\{f_k\}$ are the pole frequencies. The KT technique estimates the complex frequencies $\{\beta_k\}$ but not the complex amplitudes. The amplitudes $\{\alpha_k\}$ are later estimated using any suitable technique, such as using Total Least Squares once estimates of the poles y(n) are obtained.

The technique may be summarized as follows.

(1) Acquire N samples of the signal, $\{y^*(n)\}_{n=0}^{N-1}$ to be analyzed, where y is determined using equation 5.

(2) Construct a $L^{th}$ order backward linear predictor where $M \leq L \leq N-M$:

(a) Form a (N−L)×L Henkel data matrix, A, from the conjugated data samples $\{y^*(n)\}_{n=1}^{N-1}$.

(b) Form a right hand side backward prediction vector $h = [y(0), \ldots, y(N-L-1)]^H$ (A is the conjugate transpose).

(c) Form a predictor equation. Ab=−h, where $b=[b(1), \ldots, b(L)]^T$ are the backward prediction filter coefficients. It may be observed that the predictor implements an $L^{th}$ order FIR filter that essentially computes y(0) from y(1), ..., y(N−1).

(d) Decompose A into its singular values and vectors: $A = U\Sigma V^H$.

(e) Compute b as the truncated SVD solution of Ab=−h where all but the first M singular values (ordered from largest to smallest) are set to zero. This may also be referred to as the reduced rank pseudo-inverse solution.

(f) Form a complex polynomial $B(z) = 1 + \sum_{l=1}^{L} b(l) z^l$ which has zeros at $\{e^{-\beta_k^*}\}_{k=1}^{M}$ among its L complex zeros. This polynomial is the z-transform of the backward prediction error filter.

(g) Extract the L zeros, $\{z_l\}_{l=1}^{L}$, of B(z).

(h) Search for zeros, $Z_l$, that fall outside or on the unit circle ($1 \leq |z_l|$). There will be M such zeros. These are the M signal zeros of B(z), namely $\{e^{-\beta_k^*}\}_{k=1}^{M}$. The remaining L−M zeros are the extraneous zeros. The extraneous zeros fall inside the unit circle.

(i) Recover $s_k$ and $2\pi f_k$ from the corresponding $z_k$ by computing $\text{Re}[\ln(z_k)]$ and $\text{Im}[\ln(z_k)]$, respectively.

Figure 5:
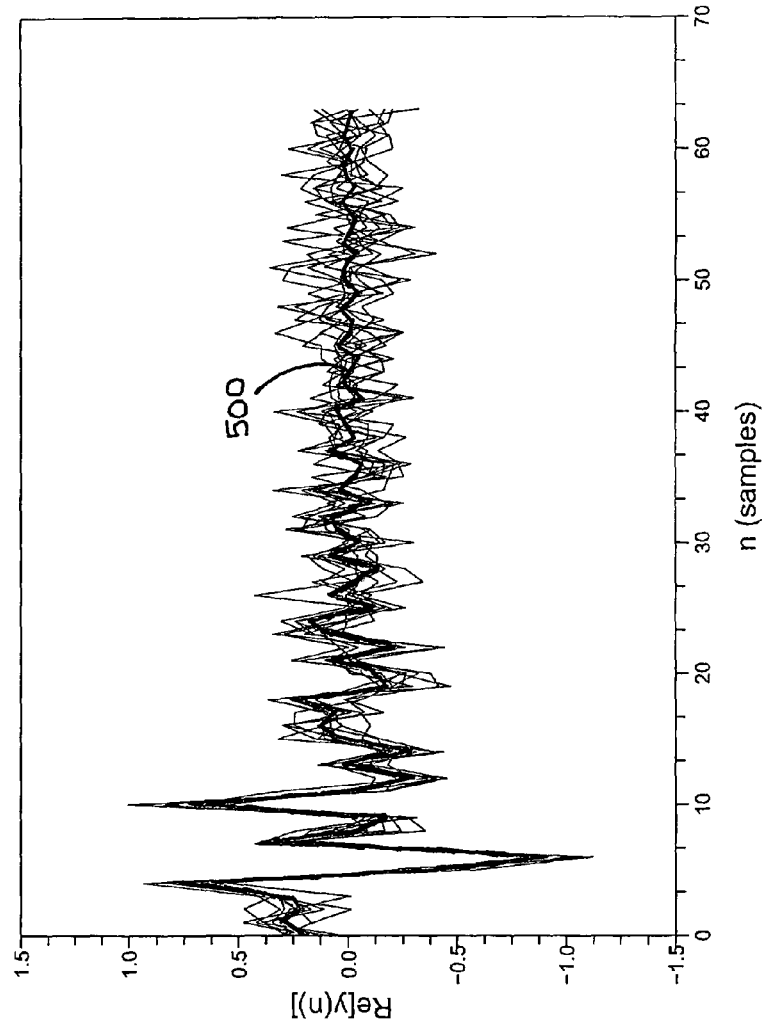
FIG. 5 illustrates noisy complex exponentials.
Figure 6:
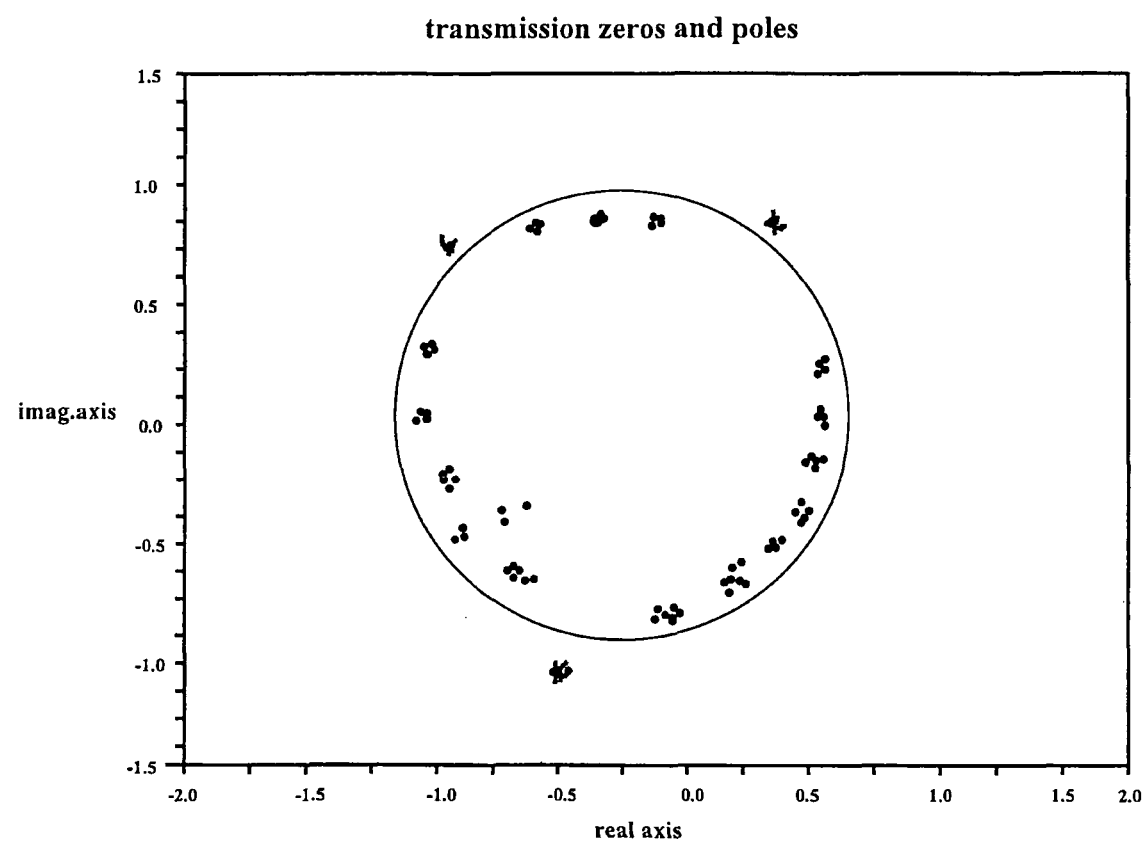
FIG. 6 illustrates transmission zeros and poles.

Referring to FIG. 5 and FIG. 6, one result of the KT technique is shown. The technique illustrates 10 instances of a 64-sample 3 pole noisy complex exponential. The noise level was set such that PSNR was about 15 dB. FIG. 5 illustrates the real part of ten signal instances. Overlaid is the noiseless signal 500.

FIG. 6 illustrates the results of running the KT technique on the noisy signal instances of FIG. 5. These results were generated with the following internal settings N=64, M=3, and L=18. The technique estimated the three single pole positions relatively accurately and precision in the presence of significant noise. As expected, they fall outside the unit circle while the 15 extraneous zeros fall inside.

As noted, the biosensor signal model defined by equation 1 accords with the KT signal model of equation 5 where M=2, $\beta_1 = 0$, $\beta_2 = -s$. In other words, equation 1 defines a two-pole signal with one pole on the unit circle and the other pole on the real axis just to the right of (1,0).

On the other hand, typical biosensor impedance signals can have decay rates that are an order of magnitude or more smaller than those illustrated above. In terms of poles, this means that the signal pole location, s, is nearly coincident with the pole at (1,0) which represents the constant exponential term B.

The KT technique recovers only the $\{\beta_k\}$ in equation 5 and not the complex amplitudes $\{\alpha_k\}$. To recover the amplitudes, the parameter estimation technique may fit the model, $$y(n) = \sum_{k=1}^{M} \alpha_k e^{\hat{\beta}_k n}.$$
$$n = 0, 1, \ldots, N-1$$

(equation 6)

to the data vector $\{y(n)\}_{n=0}^{N-1}$. In equation 6, $\{\hat{\beta}_k\}$ are the estimated poles recovered by the KT technique. The factors $\{e^{\hat{\beta}n}\}$ now become the basis function for $\hat{y}(n)$, which is parametrically defined through the complex amplitudes $\{\alpha_k\}$ that remain to be estimated. The system may adjust the $\{\alpha_k\}$ so that $\hat{y}(n)$ is made close to the noisy signal y(n). If that sense is least squares, then the system would seek $\{\alpha_k\}$ such that $\hat{y}(n)-y(n)=e(n)$ where the perturbation $\{e(n)\}$ is such that $\|e\|_2$ is minimized.

This may be reformulated using matrix notion as Ax=b+e (equation 7), where the columns of A are the basis functions, x is the vector of unknown $\{\alpha_k\}$, b is the signal (data) vector $\{y(n)\}$, and e is the perturbation. In this form, the least squares method may be stated as determining the smallest perturbation (in the least squares sense) such that equation 7 provides an exact solution. The least squares solution, may not be the best for this setting because the basis functions contain errors due to the estimation errors in the $\{\hat{\beta}_k\}$. That is, the columns of A are perturbed from their underlying true value. This suggests that a preferred technique is a Total Least Squares reformulation (A+E)x=b+e (equation 8) where E is a perturbation matrix having the dimensions of A. In this form, the system may seek the smallest pair (E,e), such that equation 8 provides a solution. The size of the perturbation may be measured by $\|E,e\|_F$, the Frobenius norm of the concatenated perturbation matrix. By smallest, this may be the minimum Frobenius norm. Notice that in the context of equation 1, $a_1=B$, and $a_2=-A$.

Figure 7:
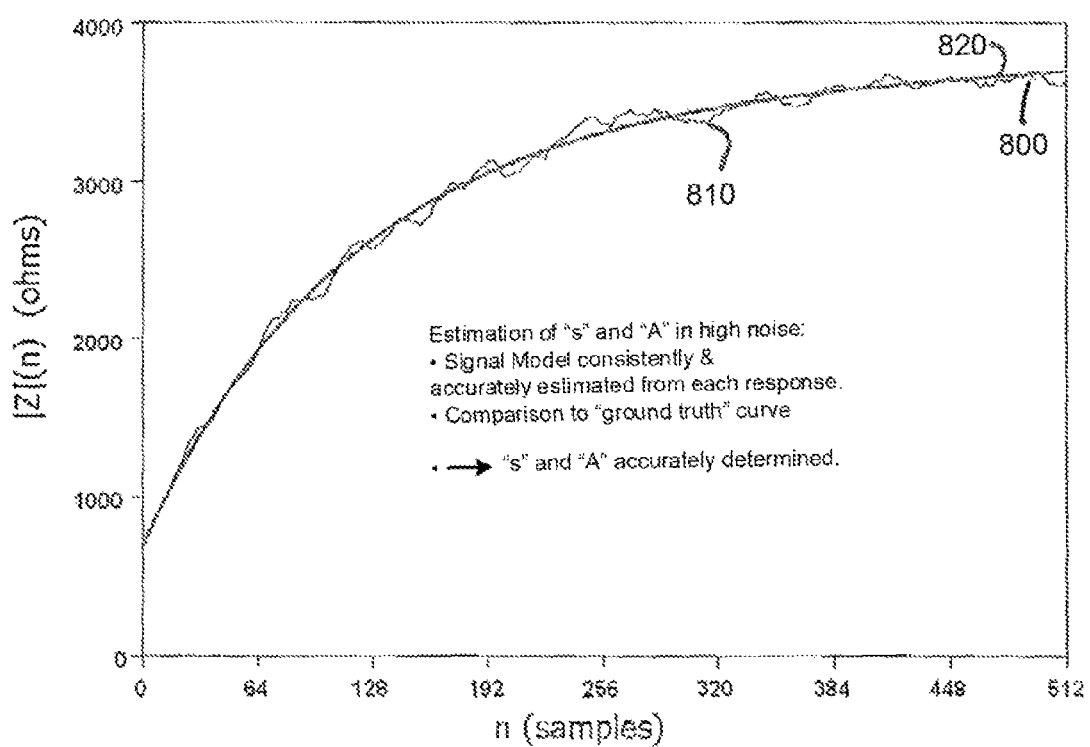
FIG. 7 illustrates a noisy signal and true signal.

The accuracy of the model parameters, (s, A) is of interest. FIG. 7 depicts with line 800 the underlying "ground truth" signal used. It is the graph of equation 1 using values for (s, A), and B that mimic those of the acquired (noiseless) biosensor impedance response. The noisy curve 810 is the result of adding to the ground truth 800 noise whose spectrum has been shaped so that the overall signal approximates a noisy impedance signal acquired from a biosensor. The previously described estimation technique was applied to this, yielding parameter estimates $(\hat{s}, \hat{A})$, and $\hat{B}$ from which the signal 820 of equation 1 was reconstituted. The close agreement between the curves 800 and 820 indicates the accuracy of the estimation.

Figure 8:
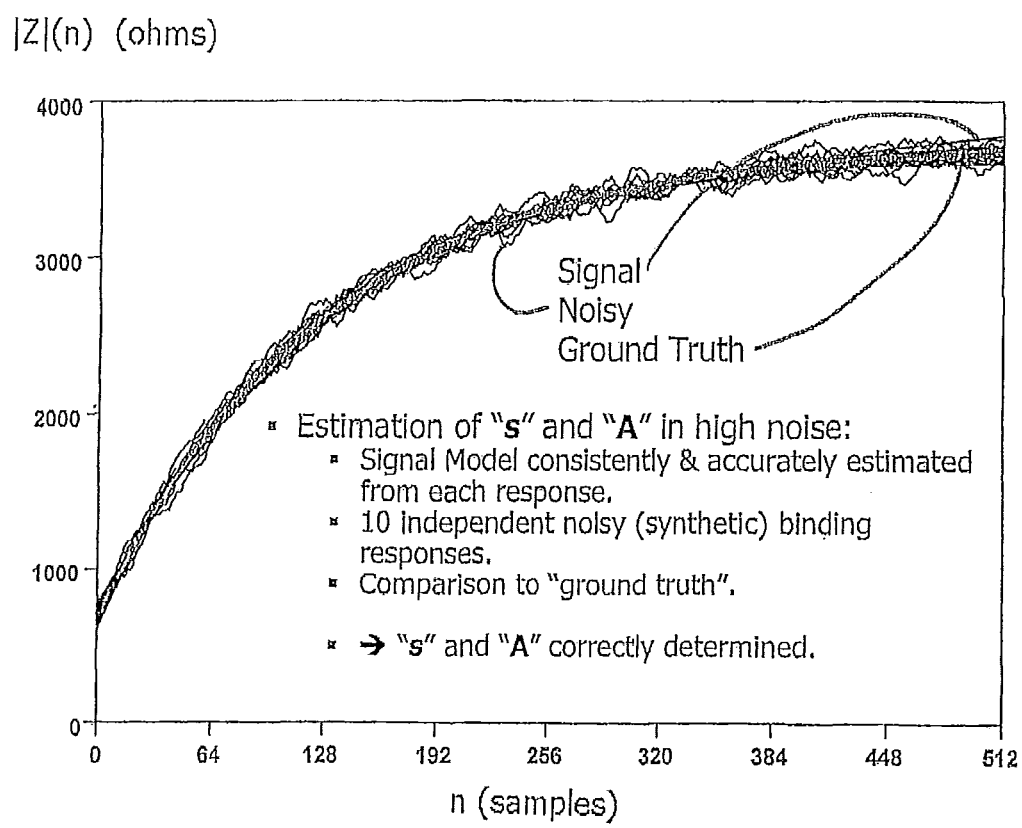
FIG. 8 illustrates multiple repetitions of FIG. 7.

FIG. 8 illustrates applying this technique 10 times, using independent noise functions for each iteration. All the noisy impedance curves are overlaid, as well as the estimated model curves. Agreement with ground truth is good in each of these cases despite the low signal to noise ratio.

Figure 9A:
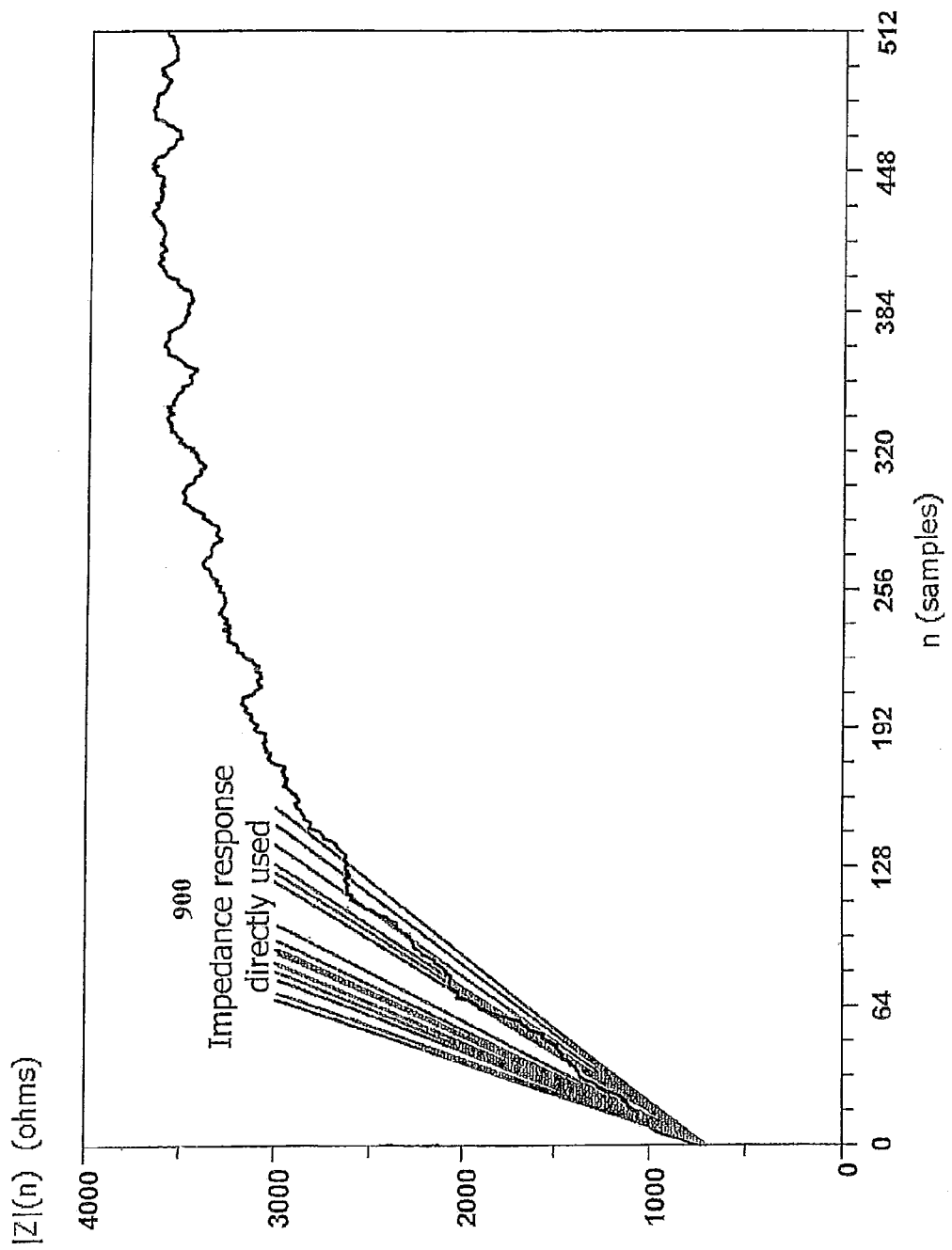
FIGS. 9A and 9B illustrate accuracy for line fitting.
Figure 9B:
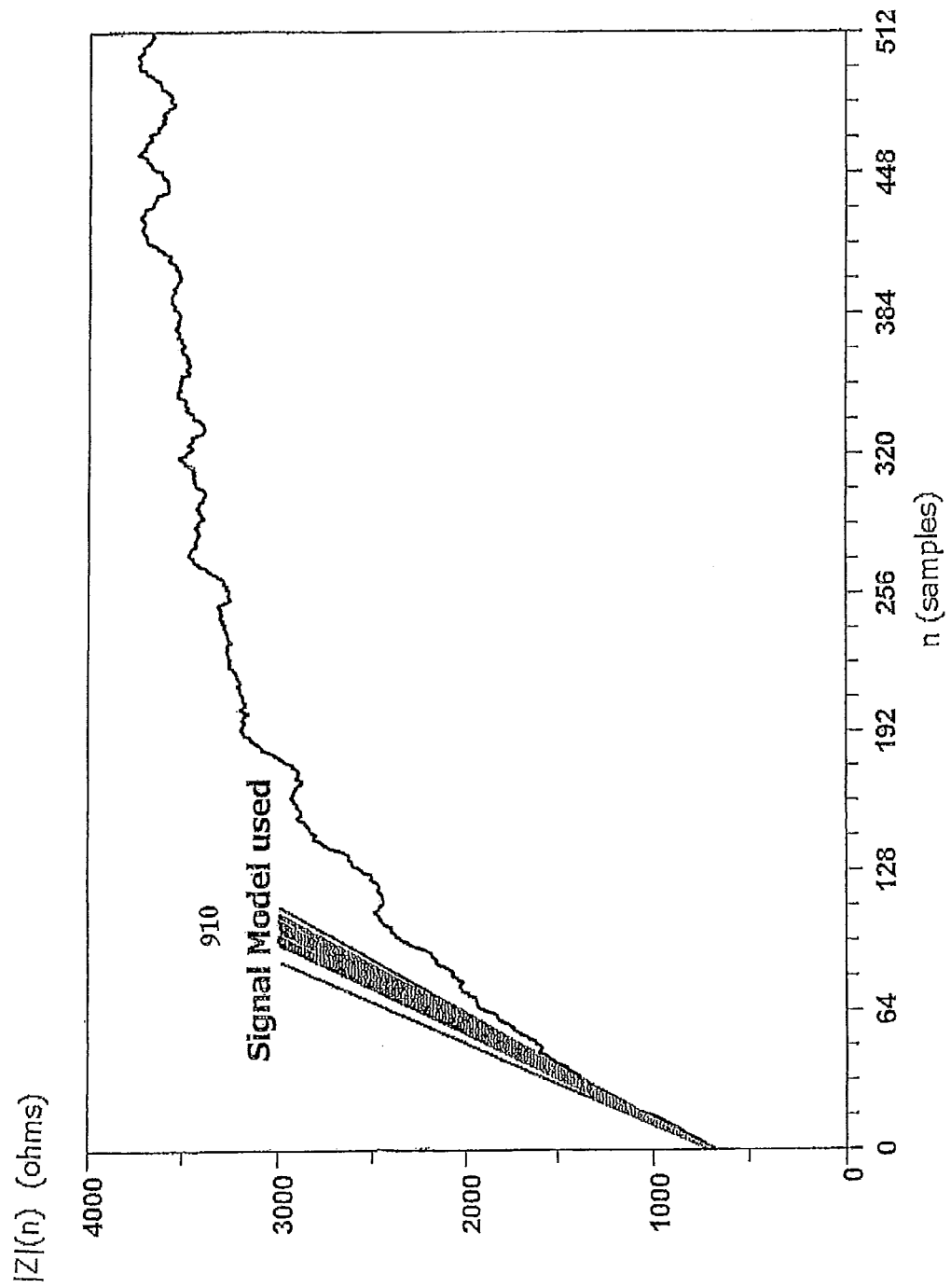

One technique to estimate the kinetic binding rate is by fitting a line to the initial portion of the impedance response. One known technique is to use a weighted line fit to the initial nine points of the curve. The underlying ground truth impedance response was that of the previous accuracy test, as was the noise. One such noisy response is shown in FIGS. 9A and 9B. Each of the 20 independent trials fitted a line directly to the noisy data 900 as shown in FIG. 9A. The large variance of the line slopes is evident. Referring to FIG. 9B, next the described improved technique was used to estimate the underlying model. Lines were then fitted to the estimated model curves using a suitable line fitting technique. The lines 910 resulting from the 20 trials has a substantial reduction in slope estimation variance. This demonstrates that the technique delivers relatively stable results.

It may be desirable to remove or otherwise reduce the effects of non-specific binding. Non-specific binding occurs when compounds present in the solution containing the specific target modules also bind to the sensor despite the fact that surface functionalisation was designed for the target. Non-specific binding tends to proceed at a different rate than specific but also tends to follow a similar model, such as the Langmuir model, when concentrations are sufficient. Therefore, another single pole, due to non-specific binding, may be present within the impedance response curve.

The modified KT technique has the ability to separate the component poles of a multi-pole signal This advantage may be carried over to the domain as illustrated in FIG. 10 and FIG. 11. Equation 9 describes an extended model that contains two non-trivial poles representing non-specific and specific binding responses ($s_1 < s_2$), $$|Z|(n) = B - A_1 e^{-s1n} - A_2 e^{-s2n} \text{ where } s_k, A_k, B \geq 0 \text{ are constants}$$

(equation 9).

Equation 9 is shown as a curve 1000 in FIG. 10 which is also close to the estimated model defined by equation 9.

Figure 13:
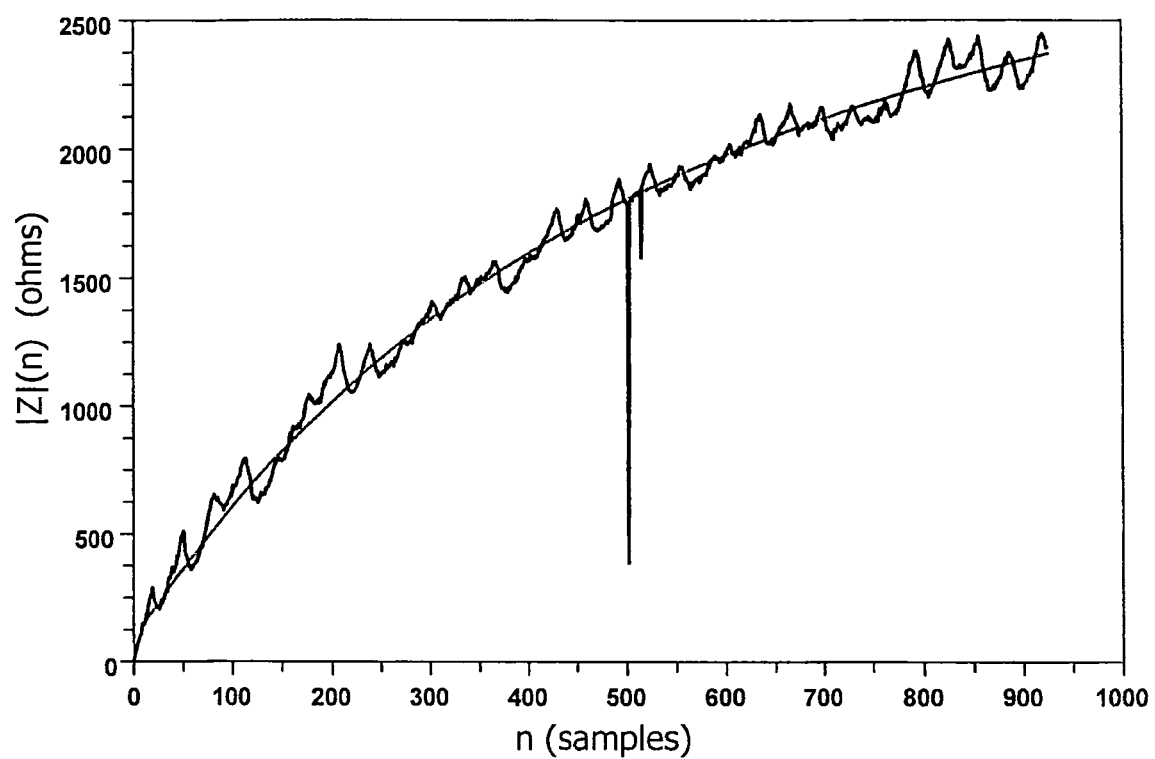
FIG. 13 illustrates low concentration impedance response curves.

FIG. 12 illustrates the impedance responses of a titration series using oligonucleotide in PBST. The highest concentration used was 5 μM. The concentration was reduced by 50% for each successive dilution in the series. In FIG. 12, the five impedance responses have been aligned to a common origin for comparison. The meaning of the vertical axis, therefore, is impedance amplitude change from time of target injection. The response model was computed for each response individually using the disclosed estimation technique. FIG. 13 plots the lowest concentration (312.5 nM) response which also is the noisiest (s=0.002695 and A=1975.3). In addition, the estimated model curve is shown which fits the data. The results of the titration series evaluation are illustrated in FIG. 14, which at low concentrations shows a relationship close to the expected linear behavior between the decay rate and the actual concentration that is predicted by the Langmuir model. For high concentrations the estimates of rate depart from linearity. At these concentrations non-ideal behavior on the sensor surface is expected.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

I claim:

1. A method for determining impedance comprising:
   (a) receiving a time varying voltage signal associated with a biosensor;
   (b) receiving a time varying current signal associated with said biosensor;
   (c) transforming said time varying voltage signal and said time varying current signal to a domain that represents complex values;
   (d) calculating a decay rate based upon said transformed time varying voltage signal and said time varying current signal.

2. The method of claim 1 wherein a discrete-time Fourier transform of said time varying voltage signal is determined.

3. The method of claim 1 wherein a discrete-time Fourier transform of said time varying current signal is determined.

4. The method of claim 2 wherein said transform is evaluated at substantially the same frequency as a driving signal of said biosensor.

5. The method of claim 3 wherein said transform is evaluated at substantially the same frequency as a driving signal of said biosensor.

6. A method for determining impedance comprising:
   (a) receiving a time varying voltage signal associated with a biosensor;
   (b) receiving a time varying current signal associated with said biosensor;
   (c) transforming said time varying voltage signal and said time varying current signal to a domain that represents complex values;
   (d) calculating an impedance representative of said biosensor based upon said transformed time varying voltage signal and said time varying current signal;
   (e) wherein a discrete-time Fourier transform of said time varying voltage signal is determined;
   (f) wherein said transform is evaluated at substantially the same frequency as a driving signal of said biosensor;
   (g) wherein a correction is applied to said time varying voltage signal in such a manner to reduce the effect of a finite time aperture.

7. A method for determining impedance comprising:
   (a) receiving a time varying voltage signal associated with a biosensor;
   (b) receiving a time varying current signal associated with said biosensor;
   (c) transforming said time varying voltage signal and said time varying current signal to a domain that represents complex values;
   (d) calculating an impedance representative of said biosensor based upon said transformed time varying voltage signal and said time varying current signal;
   (e) wherein a discrete-time Fourier transform of said time varying current signal is determined;
   (f) wherein said transform is evaluated at substantially the same frequency as a driving signal of said biosensor;
   (g) wherein a correction is applied to said time varying current signal in such a manner to reduce the effect of a finite time aperture.

8. The method of claim 6 wherein said correction reduces the effects of using non-integer number of sinusoidal cycles within said time aperture.

9. The method of claim 7 wherein said correction reduces the effects of using non-integer number of sinusoidal cycles within said time aperture.

10. The method of claim 8 wherein said correction reduces the effects of incommensurability of a sampling frequency and said frequency of said driving signal.

11. The method of claim 9 wherein said correction reduces the effects of incommensurability of a sampling frequency and said frequency of said driving signal.

12. A method for determining impedance comprising:
   (a) receiving a time varying voltage signal associated with a biosensor;
   (b) receiving a time varying current signal associated with said biosensor;
   (c) transforming said time varying voltage signal and said time varying current signal to a domain that represents complex values;
   (d) calculating an impedance representative of said biosensor based upon said transformed time varying voltage signal and said time varying current signal;
   (e) calculating a decay rate based upon said impedance.

13. The method of claim 12 further comprising calculating an amplitude based upon said impedance.

14. The method of claim 13 wherein said decay rate and said amplitude are separate from one another.

15. The method of claim 14 wherein said decay rate is not calculated based upon line fitting to a response curve.

16. A method for determining impedance comprising:
   (a) receiving a time varying voltage signal associated with a biosensor;
   (b) receiving a time varying current signal associated with said biosensor;
   (c) estimating multiple sets of amplitude and decay rate pairs from said time varying voltage signal and said time varying current signal response of said biosensor;
   (d) distinguishing between binding processes at said biosensor based upon at least two of said amplitude and decay rate pairs.

17. The method of claim 16 wherein at least one of said binding processes is a specific product bind.

18. The method of claim 17 wherein at least one of said binding processes is a non-specific product bind.

19. The method of claim 18 further comprising the steps of:
   (a) transforming said time varying voltage signal and said time varying current signal to a domain that represents complex values;
   (b) calculating an impedance representative of said biosensor based upon said transformed time varying voltage signal and said time varying current signal.

20. The method of claim 16 wherein said binding processes are specific targets that bind at different rates.

21. A method for determining impedance comprising:
   (a) receiving a time varying voltage signal associated with a biosensor;
   (b) receiving a time varying current signal associated with said biosensor;
   (c) distinguishing multiple binding rates based upon said time varying voltage signal and said time varying current signal response of said biosensor.

* * * * *

UNITED STATES PATENT AND TRADEMARK OFFICE
CERTIFICATE OF CORRECTION

PATENT NO. : 8,428,888 B2  
APPLICATION NO. : 12/661127  
DATED : April 23, 2013  
INVENTOR(S) : Dean Messing It is certified that error appears in the above-identified patent and that said Letters Patent is hereby corrected as shown below:

In the Specification

Col. 4, Line 14

Change "$M \leqq L \leqq N - M$" to read --$M \leq L \leq N - M$--;

Col. 4, Line 33

Change "$\{e^{-B^*k}\}_{k=1}^{M}$" to read --$\{e^{-B_k^*}\}_{k=1}^{M}$--;

Col. 4, Line 39

Change "$\{e^{-B^*k}\}_{k=1}^{M}$" to read --$\{e^{-B_k^*}\}_{k=1}^{M}$--;

Col. 5, Line 11

Change "$\{y(n)\}_{n=0}^{N-1}$" to read --$\{y(n)\}_{n=0}^{N-1}$--.

Signed and Sealed this  
Eleventh Day of February, 2014

Michelle K. Lee  
*Deputy Director of the United States Patent and Trademark Office*